US009498133B2

(12) United States Patent
Oraevsky et al.

(10) Patent No.: US 9,498,133 B2
(45) Date of Patent: Nov. 22, 2016

(54) OPTOACOUSTIC-ULTRASONIC SYSTEM FOR COREGISTERED FUNCTIONAL AND MORPHOLOGICAL IMAGING OF PLACENTAS

(71) Applicants: Alexander A. Oraevsky, Houston, TX (US); Sergey A. Ermilov, Houston, TX (US)

(72) Inventors: Alexander A. Oraevsky, Houston, TX (US); Sergey A. Ermilov, Houston, TX (US)

(73) Assignee: TOMOWAVE LABORATORIES, INC., Houston, TX (US)

( * ) Notice: Subject to any disclaimer, the term of this patent is extended or adjusted under 35 U.S.C. 154(b) by 0 days.

(21) Appl. No.: 14/556,316

(22) Filed: Dec. 1, 2014

(65) Prior Publication Data

US 2015/0150452 A1    Jun. 4, 2015

Related U.S. Application Data

(60) Provisional application No. 61/910,154, filed on Nov. 29, 2013.

(51) Int. Cl.
| | | |
|---|---|---|
| *A61B 5/00* | (2006.01) | |
| *A61B 5/1455* | (2006.01) | |
| *A61B 5/145* | (2006.01) | |
| *A61B 5/1464* | (2006.01) | |
| *A61B 8/14* | (2006.01) | |
| *A61B 8/08* | (2006.01) | |
| *A61B 8/00* | (2006.01) | |

(52) U.S. Cl.
CPC ........... *A61B 5/0035* (2013.01); *A61B 5/0095* (2013.01); *A61B 5/1464* (2013.01); *A61B 5/14546* (2013.01); *A61B 5/14552* (2013.01); *A61B 5/4362* (2013.01); *A61B 5/7425* (2013.01); *A61B 8/0866* (2013.01); *A61B 8/4416* (2013.01); *A61B 5/4848* (2013.01); *A61B 8/14* (2013.01); *A61B 8/4444* (2013.01); *A61B 8/5261* (2013.01)

(58) Field of Classification Search
CPC A61B 5/0035; A61B 5/7425; A61B 5/0095; A61B 5/14552; A61B 5/1455; A61B 5/14546; A61B 5/1464; A61B 5/7278; A61B 5/4848; A61B 5/4362; A61B 8/14; A61B 8/5621; A61B 8/0866; A61B 8/4444
See application file for complete search history.

(56) References Cited

U.S. PATENT DOCUMENTS

2011/0201914 A1*  8/2011  Wang .................. A61B 5/0095
                                                    600/407
2013/0109950 A1*  5/2013  Herzog ............... A61B 5/0095
                                                    600/407

* cited by examiner

*Primary Examiner* — Eric Winakur
(74) *Attorney, Agent, or Firm* — Benjamin Aaron Adler

(57) ABSTRACT

Provided herein are dual modality imaging systems and methods within displayed anatomical structures of placenta in real time. The imaging system comprises a dual modality laser optoacoustic and ultrasonic platform with a plurality of subsystems for delivering near infrared light, optoacoustic and ultrasonic pulses to the placenta and/or associated tissue and deep anatomic structures, for detecting ultrasonic pulses generated or reflected within the tissue using a multi-channel optoacoustic-ultrasound probe and associated transducers. The dual modality imaging system displays the results obtained as quantitative functional images of the parameters coregistered with anatomic tissue images. A multichannel electronic system comprising a computer tangibly storing software enables processor-executable instructions to calculate quantitative functional parameters of the placental blood within specific anatomical tissue structures and display quantitative functional optoacoustic images of the functional parameters within specific anatomical structures in the tissue that are visualized by ultrasound.

15 Claims, 5 Drawing Sheets

OPTOACOUSTIC-ULTRASONIC SYSTEM FOR COREGISTERED FUNCTIONAL AND MORPHOLOGICAL IMAGING OF PLACENTAS

CROSS-REFERENCE TO RELATED APPLICATIONS

This nonprovisional application claims benefit of priority of provisional application U.S. Ser. No. 61/910,154, filed Nov. 29, 2013, now abandoned, the entirety of which is hereby incorporated by reference.

BACKGROUND OF THE INVENTION

Field of the Invention

The present invention generally relates to the fields of biomedical imaging and obstetrics. Particularly the present invention discloses a dual modality laser optoacoustic-ultrasound imaging system (LOUIS) on a single platform that can provide medically relevant information about the developing placenta and associated tissues.

Description of the Related Art

The placenta and umbilical cord are vital for proper growth and transfer of nutrients and gases to and from the fetus. Several conditions are related to abnormal function of placenta, including abnormal fetal growth, stillbirth, preeclampsia, and preterm birth (1-2). Current in vivo methods of fetal surveillance, including ultrasound tomography (UST) techniques and fetal heart rate monitoring, have proved to have low sensitivities and high false positive rates for adverse pregnancy outcomes (3).

These techniques do not provide information on tissue oxygenation in the placenta which has important implications for both placental development as well as the development of conditions such as preeclampsia and intrauterine growth restriction (IUGR) (4-5). Doppler velocimetry of the uterine, umbilical, and middle cerebral arteries is the only clinically accepted method used during pregnancy to measure blood flow to key organs in the fetal-placental unit during pregnancy. However, oxygenation of the tissue is not measurable by ultrasound and so it is not usable to estimate local placental perfusion. Magnetic resonance imaging (MRI) and near infrared spectroscopy (NIRS) have been used experimentally to evaluate oxygenation, however, there are limitations in those approaches (6-8). Due to cost, logistics, and lack of real-time information, MRI is not feasible for surveillance of the placenta and fetus. NIRS has effectively no imaging resolution and provides only spatially integrated results.

Optoacoustic tomography (OAT) combines optical illumination and high resolution ultrasound detection to achieve deep visualization of live tissues based on optical contrast of blood, which is not degraded by light scattering (9-11). Strong near infrared (NIR) optical absorption of hemoglobin results in a superior optical contrast of blood-rich tissues (12, 13). OAT systems are substantially more cost effective alternatives to conventional MRI modalities, and have demonstrated clinical feasibility in oncology, specifically in applications related to breast and prostate cancer diagnostics (14-16). Multiple wavelengths in NIR region of optical spectra were previously used to demonstrate that OAT imaging can provide high resolution maps of total hemoglobin and blood oxygenation at frame rates close to real-time imaging (17-20). It also could be integrated with a standard clinical ultrasound imaging system such that the same probe detects ultrasonic and optoacoustic response of the tissue (15,17,21).

Thus, there is a need in the art for improved methods of monitoring placental function in vivo. Particularly, a need exists for cost effective imaging systems that can be used simultaneously with current methods of ultrasound for a real time assessment of blood oxygenation in the developing placenta and umbilical cord. Specifically, the prior art is deficient in a dual modality laser optoacoustic-ultrasound imaging system and methods of use for high contrast and high resolution visualization and coregistered functional and anatomical mapping of the placenta and associated tissue. The present invention fulfills this longstanding need and desire in the art.

SUMMARY OF THE INVENTION

The present invention is directed to a dual modality imaging system for evaluating functional parameters of placental blood within displayed anatomical structures of placenta. The dual modality imaging system comprises means for delivering near infrared light to placental vasculature and blood diffused within tissue, means for generating and delivering ultrasonic pulses to placental tissue and means for detecting ultrasonic pulses either generated within the tissue or reflected within the tissue and for producing electronic signals. The means of generating ultrasound pulses can utilize either electrical pulses applied to piezoelectric transducers or laser pulses applied to a medium with high values of optical absorption and thermoelastic expansion. The dual modality imaging system also comprises means for amplification, digitization and electronically processing said electronic signals and for calculating optoacoustic and related functional images superimposed with ultrasonic anatomic images. The dual modality imaging system further comprises means for displaying results as quantitative functional images of said blood parameters coregistered with anatomic tissue images.

The present invention also is directed to a method for evaluating functional parameters of placental blood in a subject in real time. The method comprises positioning an optoacoustic-ultrasonic probe comprising means for delivering optical pulses and ultrasonic pulses of the imaging system described herein in contact with the subject. An ultrasound tomography image of anatomical tissue structures in an area suspected for anatomical or functional abnormalities are obtained with the optoacoustic-ultrasonic probe and optoacoustic images are obtained at multiple wavelengths without a change of the optoacoustic-ultrasonic probe position. The optoacoustic images are coregistered with the ultrasound image. Quantitative functional images of a total hemoglobin [tHb] and of blood oxygenation [SO2] normalized to an optical fluence distribution at each wavelength are calculated, thereby evaluating the functional parameters of placental blood. The present invention is directed to a related method further comprising displaying an ultrasonic image of the anatomical tissue structures superimposed with the quantitative functional image of the total hemoglobin and displaying an ultrasonic image of the anatomical tissue structures superimposed with the quantitative functional image of the blood oxygen saturation. The present invention is directed to another related method further comprising diagnosing and managing a pathophysiological condition associated with the placenta and extra-placental tissue based on the evaluation of the functional parameters.

Other and further aspects, features, and advantages of the present invention will be apparent from the following description of the presently preferred embodiments of the invention given for the purpose of disclosure.

BRIEF DESCRIPTIONS OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

Figure 3:
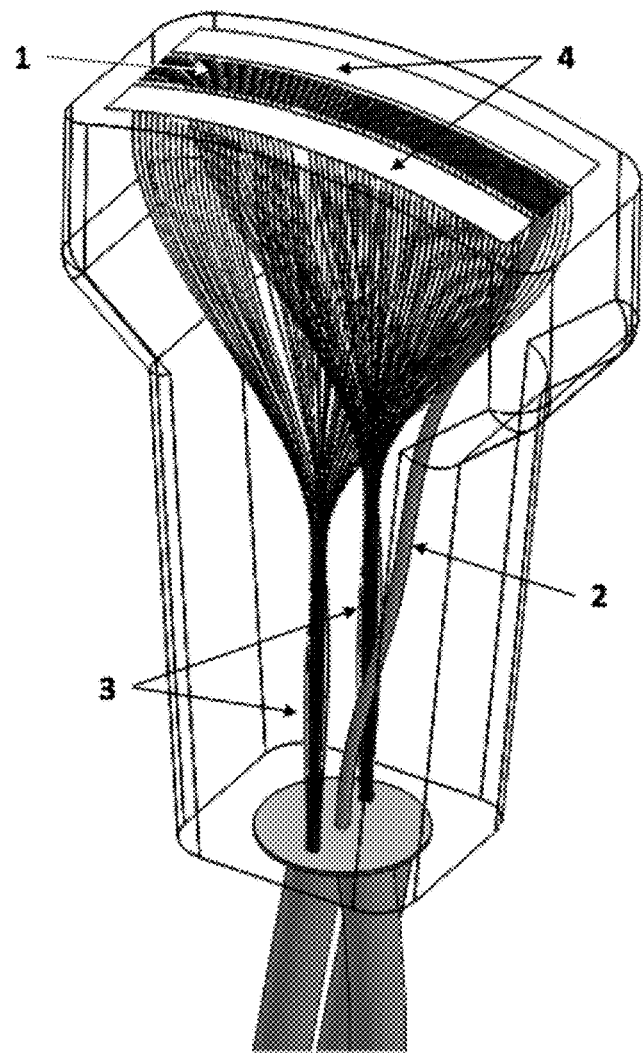

FIG. 3 is a prototype of an optoacoustic probe showing an array of ultrasonic transducers 1, electrical cable connecting ultrasonic transducers to electronic amplifiers 2, fiberoptic bundles 3, and output light bars for tissue illumination 4.

Figure 4A:
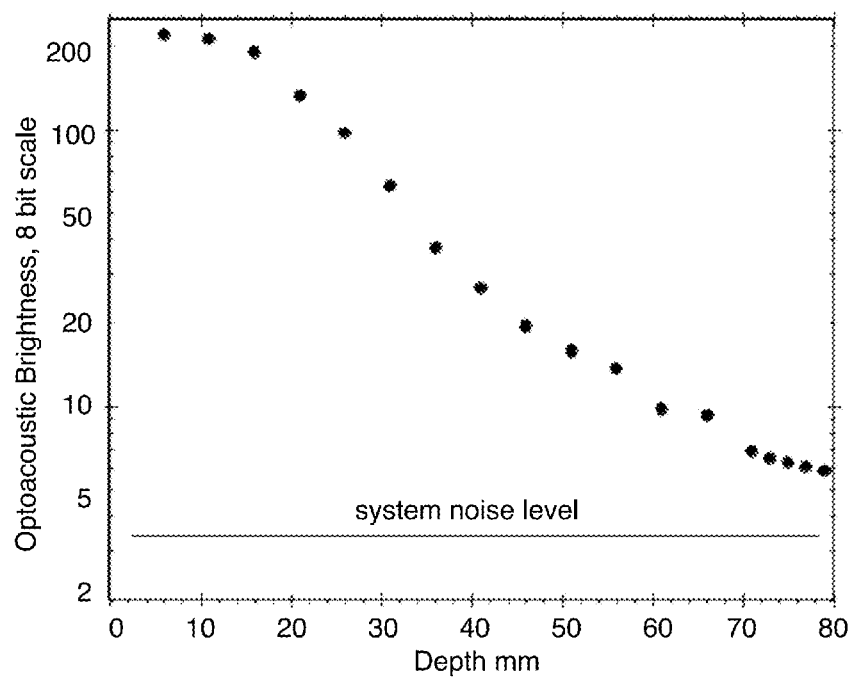
Figure 4B:
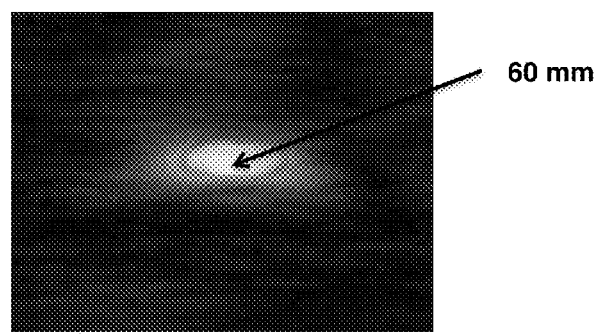

FIGS. 4A-4B illustrate optoacoustic contrast of the optoacoustic tomography image of the blood vessel inside a realistic tissue phantom comparing optoacoustic brightness with depth (FIG. 4A) and showing an image at 60 mm (FIG. 4B).

Figures 5A, 5B:
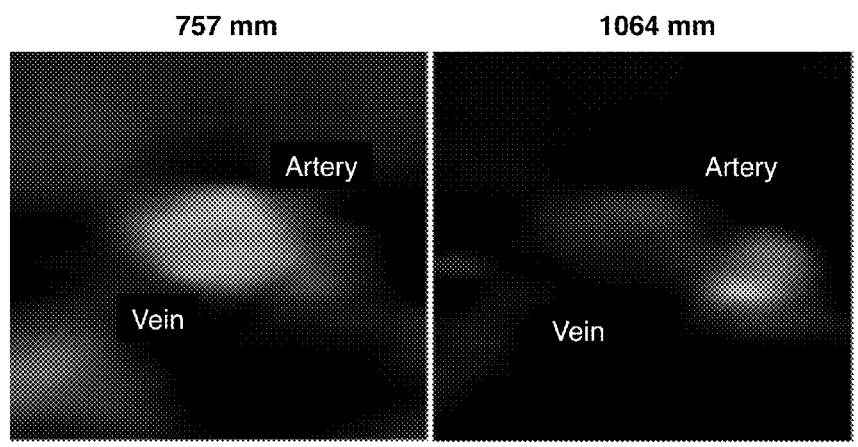

FIGS. 5A-5B are optoacoustic tomography images of live tissues with a pair of an artery and a vein at 757 nm (FIG. 5A) and 1064 nm (FIG. 5B).

DETAILED DESCRIPTION OF THE INVENTION

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "computer" or "computer system" refer to one or more machines that comprise at least a memory, a processor, a display, one or more interfaces and at least one wired and/or wireless network connection. A computer may be a desktop or laptop machine or other electronic media, for example, a smartphone or tablet, as are standard and currently known in the art. As such computer may comprise a user input device such as a keyboard, keypad, touch screen, mouse, trackball, camera, microphone, and/or other like user input device. Without being limiting, any software, modules, applications, add-ons, plug-ins, programs and/or databases, etc. and associated instructions and/or functions necessary for implementation of any imaging system or dual modality imaging system or sub-systems or means comprising the same may be programmed into the computer, may be retrieved over the network connection or may be retrieved from a non-transitory machine-readable media, such as computer readable media or storage device tangibly storing the same, may be tangibly stored in computer memory or other electronic media memory and are executable by the processor comprising the computer.

As used herein, the term "subject" refers to a female mammal or woman, particularly a pregnant woman.

As used herein, the term "LOUIS" refers to a Laser Optoacoustic Ultrasound (Ultrasonic) Imaging System as a dual modality.

In one embodiment of the present invention there is provided a dual modality imaging system for evaluating functional parameters of placental blood within displayed anatomical structures of placenta, comprising means for delivering optical pulses of near infrared light to blood in placental tissue and vasculature; means for generating and delivering ultrasonic pulses to placental tissue; means for connecting and assembling both of said delivery means within a hand-held probe; means for detecting ultrasonic pulses either generated within the tissue or reflected within the tissue and for producing electronic signals; means for amplification, digitization and electronically processing said electronic signals and for calculating optoacoustic and related functional images superimposed with ultrasonic anatomic images; and means for displaying results as quantitative functional images of said blood parameters coregistered with anatomic tissue images.

In one aspect of this embodiment the means for delivering near infrared light may comprises a pulsed laser operable at multiple wavelengths within a near-infrared spectral window, where the laser is rapidly switchable between different wavelengths in the spectral window and a fiberoptic light delivery system having a fused circular input tip operable for maximum transmission and randomized output for homogenous illumination. In this aspect the wavelengths in the near infrared spectral window may be of a maximum tissue transparency and be within an absorption spectrum of hemoglobin and oxy-hemoglobin. Particularly, the near infrared spectral window may comprise wavelengths of about 750 nm to about 840 nm.

In another aspect the means for generating and delivering ultrasonic pulses to placental tissue may comprise electrical pulses applied to piezoelectric transducers. Alternatively, the means for generating and delivering ultrasonic pulses to placental tissue comprises laser pulses applied to a layer of material with a strong optical absorption and strong thermoelastic expansion.

In yet another aspect the means for delivering optical pulses and delivering and detecting ultrasonic pulses may comprise a multichannel optoacoustic-ultrasonic probe operable to detect ultrasonic pulses from a depth of tissue within an ultra-wide band of ultrasonic frequencies. In this aspect the multichannel optoacoustic-ultrasonic probe may be a handheld transabdominal optoacoustic ultrasonic probe or a handheld transvaginal optoacoustic ultrasonic probe. In this aspect the ultrawide-band of frequencies may be about 100 kHz to about 10 MHz.

In yet another aspect the means for the means for electronically processing said ultrasonic pulses and means for displaying the results comprise a multichannel electronic system having low noise ultrawide-band analog amplifiers, analog to digital converters and digital data acquisition, where the multichannel electronic system is operable to detect, amplify, digitize, process, and store optoacoustic and ultrasonic signals produced by the optical and ultrasonic pulses generated within the blood or tissue or both; and a computer in electronic communication with the multichannel electronic system and having at least one memory, processor, display, and network connection tangibly storing software comprising processor-executable instructions to calculate quantitative functional parameters of the placental blood within specific anatomical tissue structures; and display quantitative functional optoacoustic images of the functional parameters within specific anatomical structures in the tissue that are visualized by ultrasound.

In this aspect the processor-executable instructions are executable to obtain an ultrasound tomography image of the placenta or associated tissue in an area suspected for anatomical or functional abnormalities; to obtain optoacoustic images using at least two wavelengths without a change of the optoacoustic-ultrasonic probe position; to coregister the optoacoustic images with the ultrasound image; to calculate quantitative functional images of a total hemoglobin [tHb] and of blood oxygenation [SO2] normalized to an optical fluence distribution at each wavelength; to display an ultrasonic image of anatomical tissue structures superimposed with the quantitative functional image of the total hemoglobin; and to display an ultrasonic image of the anatomical tissue structures superimposed with the quantitative functional image of the blood oxygen saturation.

In this embodiment and all aspects the quantitative functional parameters may comprise total hemoglobin and oxygen saturation. Also, the tissue may comprise placenta or umbilical cord or both. In addition, the quantitative functional parameters may be evaluated in real time within at most 100 milliseconds.

In another embodiment of the present invention there is provided method for evaluating functional parameters of placental blood in a subject in real time, comprising the steps of positioning an optoacoustic-ultrasonic probe comprising means for delivering optical pulses and ultrasonic pulses of the imaging system as described supra in contact with the subject; obtaining an ultrasound tomography image of anatomical tissue structures in an area suspected for anatomical or functional abnormalities with the optoacoustic-ultrasonic probe; obtaining optoacoustic images at multiple wavelengths without a change of the optoacoustic-ultrasonic probe position; and coregistering the optoacoustic images with the ultrasound image; and calculating quantitative functional images of a total hemoglobin [tHb] and of blood oxygenation [SO2] normalized to an optical fluence distribution at each wavelength, thereby evaluating the functional parameters of placental blood.

Further to this embodiment the method comprises displaying an ultrasonic image of the anatomical tissue structures superimposed with the quantitative functional image of the total hemoglobin; and displaying an ultrasonic image of the anatomical tissue structures superimposed with the quantitative functional image of the blood oxygen saturation. In another further embodiment the method comprises diagnosing and managing a pathophysiological condition associated with the placenta and extraplacental tissue based on the evaluation of the functional parameters. Examples of the conditions are abnormal perfusion and oxygenation, placental abruptions or are associated with effects of medications, smoking or exercise. In all embodiments the anatomical tissue structures may be the placenta, the umbilical cord or both. Also, in all embodiments the multiple wavelengths may comprise a near infrared spectral range of about 750 nm to about 840 nm.

Provided herein is a cost-effective laser optoacoustic (OAT) system combined on a single platform with an ultrasound tomography (UST) system for high contrast and high resolution visualization and coregistered functional and spatially-resolved anatomical mapping and morphological evaluation of the placenta and associated tissue, for example, the umbilical cord, in pregnant women. In the optoacoustic-ultrasound multiple optical wavelengths are used for transabdominal or transvaginal illumination of the placenta to obtain quantitative functional maps of blood distribution and oxygen saturation at a video frame rate of real-time imaging. Fully integrated and coregistered with medical ultrasound the imaging system enables clear identification of changes in functional blood perfusion and oxygenation within specific tissue structures.

Generally, a dual modality imaging system comprises means or subsystems for 2D or 3D optoacoustic imaging using a pulsed laser and a hand-held probe, such as, but not limited to, a multichannel optoacoustic-ultrasonic probe that allows accurate quantitative assessment of local oxygenation in placenta. A means or subsystem for delivering near infrared light may comprise a pulsed laser and fiber optic system. The pulsed laser is operable at multiple wavelengths, for example, but not limited to, within a near infrared spectral range of about 750 nm to about 840 nm, and delivers the near infrared light to the placenta, placental vasculature and blood. Wavelengths within this near infrared spectral window are of maximum tissue transparency and are within an absorption spectrum of hemoglobin and oxyhemoglobin. Moreover, the pulsed laser can be rapidly switched to different wavelengths. A fiber optic light delivery system may comprise a fused circular input tip operable for maximum transmission and for randomized output to provide homogenous illumination.

The dual modality imaging system comprises means or subsystems that are configured to generate and deliver ultrasonic pulses to placental tissue via, for example, electrical pulse applied to transducers, such as, but not limited to, piezoelectric transducers. Alternatively, laser pulses may be applied to a layer of material that has a strong optical absorption and a strong thermoelastic expansion. Examples of such materials include thin layer of black PDMS (alternatively PMMA filled with absorbers) polymer embedded with highly concentrated absorbers—carbon nanotubes, strongly absorbing in the near-infrared and having high thermal expansion coefficient.

Another subsystem of the dual modality imaging system comprises means for delivering optical pulses, means for delivering ultrasonic pulses and means for detecting ultrasonic pulses, for example, a multichannel optoacoustic-ultrasonic probe. The multichannel probe may be a handheld probe, for example, a transabdominal probe or a transvaginal probe configured to deliver optical pulses and ultrasound pulses to deep tissue. The hand-held probe can deliver pulses to tissue at a depth greater than 60 mm with an excellent in vivo resolution of less than 0.5 mm and can detect ultrasonic pulses produced within the tissue or anatomic structures thereof. This is enhanced with ultrawideband ultrasonic imaging utilizing frequencies of at least 100 kHz, preferably about 100 kHz to about 10 MHz. The transducers may comprise, but are not limited to, an ultrasound detection array of ultrawide-band ultrasonic transducers. The ultrasound detection array provides the dual modality imaging system or LOUIS with resolution sufficient to differentiate individual microvessels.

In addition the imaging system comprises means or subsystems for electronically processing and displaying imaging data. A multichannel electronic system includes components and/or modules that include, but are not limited to, low noise ultrawide-band analog amplifiers, analog to digital converters and digital data acquisition. The multichannel electronic system is configured or operable to detect, amplify, digitize, process, and store optoacoustic and ultrasonic signals produced by the optical and ultrasonic pulses generated within the tissue or anatomic structures thereof or both.

A computer is in electronic communication with the multichannel electronic system and, as is standard in the art, comprises at least one memory, processor, display, and network connection. The computer memory tangibly stores software comprising processor executable instructions to perform various functions. For example, the processor executable instructions may function to calculate quantitative functional parameters of the placental blood within specific anatomical tissue structures and to display quantitative functional optoacoustic images of the functional parameters within specific anatomical structures in the tissue that are visualized by ultrasound.

More particularly, the software is configured to enable real-time coregistered functional and anatomical mapping of placenta and operates to obtain an ultrasound tomography image of the placenta or associated tissue in an area suspected for anatomical or functional abnormalities and, without changing the optoacoustic-ultrasonic probe position, to obtain optoacoustic images at multiple wavelengths, i.e., at least two, whereupon the optoacoustic images are coregistered with the ultrasound image. Then quantitative functional images of a total hemoglobin [tHb] and of blood oxygenation [SO2] normalized to an optical fluence distribution at each wavelength are calculated. Furthermore, ultrasonic images of the anatomical tissue structures are superimposed with the quantitative functional images of the total hemoglobin and of the blood oxygen saturation.

The dual modality imaging systems described herein demonstrate high resolution real-time optoacoustic imaging of intra- and extraplacental blood content and high resolution real-time optoacoustic imaging of placental blood oxygenation. Both imaging outputs are mapped on the morphological structures as they are seen on a conventional transabdominal ultrasound. The coregistered images provide spatially resolved maps showing details of blood perfusion, oxygenation and morphological features of placenta in real time. Moreover, it is contemplated that the dual modality imaging systems described herein may comprise laser generated ultrasound for higher image resolution to image placentas during early pregnancy.

Also provided herein are methods for evaluating a functional quantitative parameter of placental blood in anatomic structures in the placenta or associated tissue such as the umbilical cord via the imaging systems described herein. The method enables the structural ultrasonic and functional optoacoustic images obtained thereby to naturally coregister, which enhances the value of the diagnostic information available in the dual modality LOUIS imaging systems as compared to stand alone clinical ultrasound systems.

Methods utilizing the optoacoustic-ultrasonic imaging dual modality have significant value in everyday OB/GYN clinical practice to improve diagnosis and management of pathophysiological conditions related to abnormal perfusion and oxygenation within the placenta and extraplacental tissue, early identification of abruptions and other problems during pregnancy. In addition, the optoacoustic-ultrasonic imaging dual modality expands the instrumentation available for clinical research in placental function. For example, the dual modality imaging systems would aid in clinical research to understand the effects caused by medications, smoking, and exercise on long and short term placental function.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

LOUIS Imaging System

Figure 1:
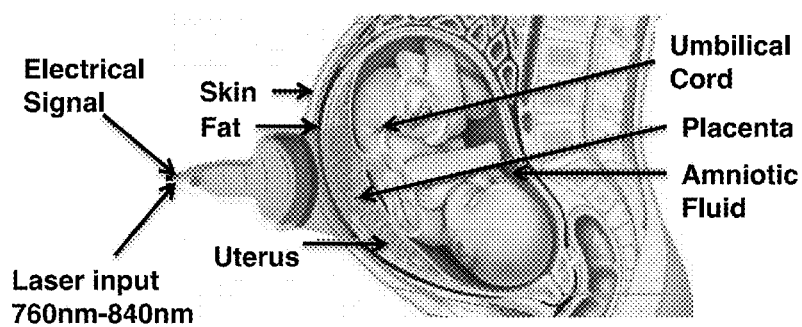
FIG. 1 illustrates the combined dual modality of laser optoacoustic-ultrasonic imaging system (LOUIS) for evaluation of functional parameters of blood in placenta within specific anatomical tissue structures.

FIG. 1 illustrates the LOUIS imaging system which is configured or enabled for high resolution real-time optoacoustic imaging of intra- and extraplacental blood perfusion, for high resolution real-time optoacoustic imaging of placental blood and oxygenation and for mapping the functional information of perfusion and oxygenation onto the morphological structures that is visualized concurrently using transabdominal or transvaginal ultrasound. More particularly, the figure illustrates:

1) an ultrasonic probe upgraded with light delivery system;

2) OAT Data Acquisition Board (DAB) and software that works either in "sequence" mode or in a "toggling" acquisition mode with ultrasound; and 3) an additional laser unit that provides Q-switched fiber optically coupled output in a near infrared optical range or spectral window of about 750-840 nm.

EXAMPLE 2

Figure 2:
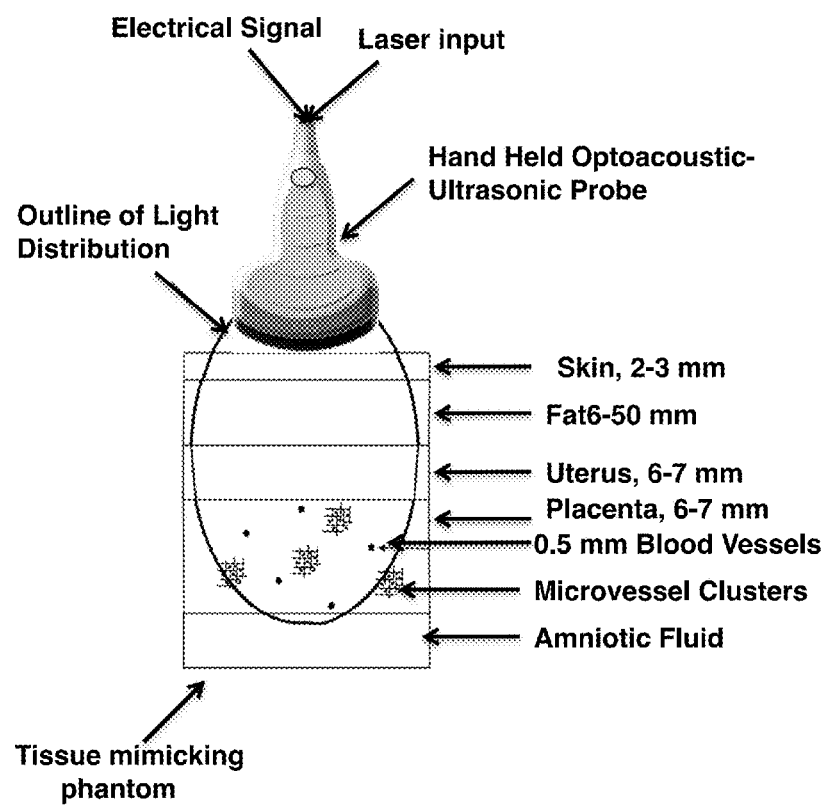
FIG. 2 illustrates a tissue mimicking digital phantom for modeling and simulation of imaging placenta with dual modality optoacoustic ultrasonic probe.

Digital Phantoms for Computer Simulations of Transabdominal Optoacoustic Imaging of Placenta Digital phantoms are utilized for Monte Carlo based simulations of OAT imaging. A typical digital OAT phantom is a 3D map of optical properties which simulates a portion of the body affected by illumination during an OAT imaging procedure. Special care is taken with respect to boundary conditions by accounting for optical continuity of deep tissues and by modeling physical contact of the skin and optoacoustic probe. The digital phantoms utilized herein have a stratified geometry with individual layers representing skin, adipose tissue, uterus, placenta, and amniotic fluid (FIG. 2). The thickness of each layer is either obtained from published reference data or is estimated from at least 10 transabdominal ultrasonic images acquired during routine clinical examinations of the placenta at various gestational ages.

Each layer, except for the placenta, is represented as a homogeneous medium with optical properties for a particular wavelength obtained either directly from published references or indirectly by assuming that NIR optical absorption comes predominantly from blood, and using volumetric fractions of blood known for each particular tissue layer. The placental layer is populated either with 0.5 mm blood vessels for resolution studies or with clusters of 0.1 mm microvessels for studies of blood content and oxygenation levels. All 0.5 mm blood vessels are oriented orthogonally to the imaging plane of the probe to provide reference circular objects on the reconstructed OAT images. All 0.1 mm blood vessels inside the clusters are randomly distributed along 3 orthogonal axes. The average density of blood vessels and microvessels within placenta is designed for consistency with published data on the volumetric blood fraction in the placenta. The density of microvessels inside a particular cluster is varied to ±50% that of the average. Oxygen saturation of blood inside both 0.5 mm vessels and microvessel clusters is varied between 50 and 100% with increments of 0.05.

Multiwavelength optical illumination is used to evaluate spatial distribution of blood oxygenation. An NIR optical range of about 750-840 nm was selected centered at the isosbestic point of hemoglobin (802 nm) where oxy- and deoxy-forms equally absorb optical energy (12, 22). Near-infrared spectroscopy (NIRS) that measures oxygen saturation without spatial resolution utilizes 3-5 wavelengths of NIR optical radiation in the similar range (13, 23, 24). The same range is used in optoacoustic spectroscopy of blood (18, 20, 25-27). In order to maintain the balance between the accuracy of the measured oxygen saturation, the ability to perform real-time imaging, and the cost of the system the number of utilized wavelengths was limited to 3-5. The digital phantoms with the placenta represented by 0.5 mm blood vessels is created for 3 wavelengths in the range of about 750-840 nm with an equal step of 40 nm. The digital phantoms with placenta represented by microvessel clusters are created for 5 wavelengths in the range of about 750-840 nm with an equal step of 20 nm. A total of 8 different digital phantoms were developed and tested.

EXAMPLE 3

Optimization of Shape, Size, and Arrangement of the Optical Fibers within Standard Transabdominal Ultrasound Probe Using Monte Carlo Computer Simulation of Optoacoustic Imaging and Digital Phantom Optical illumination is critical for good quality 2D or 3D optoacoustic imaging. Conventionally it is achieved using two fiber optic bundles shaped at the output termini in a rectangular pattern and attached on both sides of the ultrasound probe (FIG. 3). Two illumination modes, dark field and bright field, have been employed currently for 2D OAT imaging. Dark field is formed when light bars are significantly separated from the imaging plane of the probe. In that case OAT image is formed by backscattered light. Such an approach significantly limits the depth of view and is not practical for imaging tissue that is deeper than 1 cm. The bright field mode is formed by forward scattered photons. It is traditionally used in clinical applications for 2D OAT imaging of breast and prostate (16, 17). Bright field illumination for imaging the placenta is used herein since typical depth of the placenta on ultrasound images is on the order of 15-30 mm. Additional parameters to consider in development of OAT illumination are shape and size of the light bar cross-section and its distance from the imaging plane. Wider light bars provide more homogeneous illumination in the bright field, but require more laser energy considering constraints imposed by the maximum permissible skin exposure of about 20 mJ/$cm^2$ for the selected NIR range (28).

An advanced laser system (SpectraWave 2X, TomoWave Laboratories, Inc., Houston, Tex.) was developed for breast imaging applications and provides up to 200 mJ/pulse in the 750-840 nm range. Conservatively, considering that losses in fiber optics could be up to 50%, a top estimate of 100 mJ/pulse for two light bars, which limits the cross-section of each light bar to 2.5 $cm^2$ to achieve maximum sensitivity was utilized. The length of the light-bars is adequate to prevent shadows at the edges of the field of view on OAT images. For a linear ultrasound probe the selected length is usually equal or slightly longer than the array of transducers. Computer simulations are performed to determine the optimal length of the light bars for the transabdominal convex ultrasonic probe.

In the past, we developed our own OAT imaging simulation software that works with a variety of light delivery systems, acoustic arrays, and DAB systems. It was used and described in our previous peer-reviewed publications (14, 16). Three digital models with 0.5 mm blood vessels in placental layer (see Embodiment 1.1 above) is utilized to optimize optoacoustic illumination. The problem in deep tissue OAT imaging comes from sensitivity decreasing with the size of a target and depth which is due to diffraction of optoacoustic waves (9). A large number of array elements, such as, but not limited to, at least 64, is essential to improve sensitivity of the system. A commercial ultrasound probe with 128 elements is used herein.

Another problem typically encountered in deep tissue OAT imaging is a large dynamic range of the signals caused by optical attenuation, which is on the order of 2.3 times per centimeter of tissue (29). Since only the placenta and some immediately adjacent tissue, e.g., the uterus and amniotic fluid, is visualized, the reconstructed depth of view does not exceed 10 mm, i.e. reconstructed images are 40 mm×10 mm. The images of blood vessel targets are analyzed for OAT contrast and resolution. The most practical design, which achieves at least 1 mm resolution for blood vessel targets in all the phantoms is implemented in the probe.

EXAMPLE 4

Multiwavelength Optoacoustic Imaging Methodology for Quantitative Measurements of Local Blood Content and Oxygenation Levels in Placenta Five digital models with placental microvessel clusters as in Example 2 and a probe design optimized in Example 3 are used. Both oxygenated and deoxygenated blood absorbs well in the NIR range of about 760-840 nm. Optical absorption contrast with respect to background tissue is about 50:1 (12, 29). However, all optical methods that claim quantitative metrology of absorption in live tissue, and therefore concentration of chromophores (for 750-840 nm, just hemoglobin), run into an extremely challenging problem of unknown spatial distribution of optical fluence. One way to overcome this problem is implemented in diffuse optical tomography, which relies on a light propagation model for biological tissues to get spatially averaged optical absorption characteristics (13, 24). This problem of unknown fluence is overcome by using coefficient of the local contrast, $K_{PU}$, between the placenta and the uterus as a diagnostic metric of blood content:

$$K_{PU} = \frac{I_P}{I_U} \approx \frac{[Hb^T]_P}{[Hb^T]_U}, \quad \text{(Eq. 1)}$$

where l indicates local intensity on OAT image at the region of interface inside placenta (index P) and uterus (index U); [HbT]=[HbO]+[Hb] is the concentration of total hemoglobin. What justifies equation (1) is the assumption that over the uterus-placenta interface change of optical fluence is much smaller than that of optical absorption. The Monte Carlo models are used to validate that assumption for a physiological range of optical properties inside the uterus and placenta. Since equation (1) has a fluence-free ratiometric form, it is independent of wavelength. Therefore, multiple wavelength data could be simply averaged to increase accuracy of evaluation of $K_{PU}$. Using Monte Carlo simulations the minimum number of wavelengths required to evaluate $K_{PU}$ with accuracy of 10% is determined.

Local blood oxygenation in the placenta is evaluated using principles of multiwavelength optoacoustic spectroscopy (18). Wavelength dependent blood oxygenation parameter ($P_{SO2}$) is calculated for all possible permutations of wavelength pairs (i,j):

$$P_{SO2}(x, z)_{i,j} = \frac{I(x, z)_i}{I(x, z)_j}. \quad \text{(Eq. 2)}$$

Then the minimization problem is solved for the known spectral relationship between the blood oxygenation parameter and blood oxygenation index:

$$sO_2 = \frac{[HbO]}{[HbO] + [Hb]}. \quad \text{(Eq. 3)}$$

Using Monte Carlo simulations we determine the minimum number of wavelengths required to evaluate SO2 in the placenta with an accuracy of 10% is determined.

EXAMPLE 5

Integration of a Standard Transabdominal Ultrasound Probe with Fiberoptic Bundles A preclinical prototype of the LOUIS system is fabricated using the hybrid probe and existing electronics for optoacoustic and ultrasonic imaging. The design is based on minimal modifications to a clinical general-purpose ultrasound imaging system. In one significant modification the light delivery module is integrated into the transabdominal imaging probe to enable optoacoustic imaging in a backward bright-field illumination mode. The light delivery module consists of a single bifurcated (1-in-2) optical fiber bundle with output termini shaped in rectangular patterns and curved according to the shape of the used probe. The arrangement of individual output fibers in each terminal is randomized with respect to the input in order to provide homogeneous illumination without dangerous "hot spots". Fiber bundle outputs are integrated into the convex transabdominal probe housing on both sides (FIG. 3) according to the design optimized in the Monte Carlo simulations of Example 3 and similar to the previously established linear breast probe (17). The fiber bundle outputs are acoustically isolated from the sensitive elements of the probe in order to avoid significant imaging artifacts caused by ultrasound optically generated inside the housing. The fiber bundle input is optically coupled to the Ti:Saph laser output tunable in the range of about 750-840 nm. A LOUIS 128-ch data acquisition (DAQ) module (TomoWave Laboratories, Inc., Houston Tex.), which is universal across a variety of biomedical applications of array-based optoacoustic imaging (14, 16, 30-32), is used. It incorporates 128 parallel channels of wideband electronics with analog amplification up to 90 dB, digital sampling of 40 MHz up to 1536 samples per channel, and 10 Hz imaging frame rate. The developed optoacoustic imaging unit is evaluated to assure that incident fluence is consistent with the requirements of the ANSI Z136.1 Laser Safety Standard (28).

The acousto-electric impulse response of the system is measured using an in-house system that is modified to accommodate a convex handheld probe. The system can be designed with separate OAT and UST DAQ modules, but a preferred system has a combined OAT/UST electronics. Ultrasound and multiwavelength optoacoustic imaging is queued or toggled. Thus, a commercial version of the prototype comprises a fully integrated clinical dual modality probe and DAB that allows real-time toggling between OAT and UST frames and that provides real-time evaluation of blood content and oxygenation with the placenta.

EXAMPLE 6

Creation of Software that Displays Blood Content and Oxygenation Maps of Placenta Previous development of real-time OAT imaging to enable data processing and tomographic reconstruction, which are appropriate for the convex probe geometry is utilized. Current software is based on Matlab and C++ for 2D optoacoustic-ultrasonic imaging of a breast with linear handheld probes. Using methodology developed in Example 4, Matlab software is created that displays maps of local blood contrast ($K_{PU}$) and blood oxygenation index (SO2) inside the placenta. Image presentation is optimized either for composite overlay on the standard clinical ultrasound images or for standalone panels of functional information coregistered with ultrasound. Algorithms tested in the research Matlab environment in commercial grade C++ and CUDA based code are implemented. Previously tested and verified commercial grade C++ DAB kernel of LOUIS is used in the system provided herein.

EXAMPLE 7

Development of Stratified Tissue Simulating Phantoms that are Adequate for Optoacoustic and Ultrasonic Imaging of Placenta at Different Levels of Local Blood Perfusion and Oxygenation Optoacoustic and ultrasonic phantoms for breast and prostate imaging are known in the art (14, 16). Phantoms in this project simulate multilayered structures as they are seen on clinical ultrasound imaging of placenta and consistent with digital phantoms implemented in Example 2 (FIG. 2). Gelatin is one of the most traditional materials for mimicking optical and acoustic properties of live tissues. It is used for matrix of all the layers except for placenta with optical, and acoustic properties simulating corresponding tissues. There is a technology for manufacturing OAT phantoms that mimic properties of the breast (33) which can be modified easily to produce the required OAT phantoms of abdominal tissues. Optical properties of individual layers are measured using an integrating sphere (34). Phantoms are created that have a scattering background with an effective attenuation coefficient of about 1-1.2 cm$^{-1}$ and a reduced scattering coefficient about 10 cm−1 consistent with live tissue (29). The necessary spectral characteristics of optical absorption in the uterus layer is achieved by mixing hemoglobin into a gelatin matrix. The placenta is modeled using a well-established ex vivo placental perfusion system (35-38).

Briefly, the perfusion system comprises a perfusion chamber, a maternal and fetal reservoir, two peristaltic roller pumps and two magnetic stirring devices that are connected together via tubing establishing a functional perfusion chamber. The placenta vascular network is perfused by simultaneous perfusion of the fetal and maternal circulation of one villous tree while the fetal flow is established by cannulation of a chorionic artery and vein pair supplying one cotyledon with Krebs Ringer. During OAT imaging experiments, the placenta is placed immediately in contact with the uterus layer of the gelatin phantom that simulates in vivo imaging conditions. The perfusion chamber is then placed in a heated (37° C.) flowbench prior to acquiring optoacoustic images of placenta tissue under different conditions. Term placentas are collected from uncomplicated pregnancies and births after elective caesarean sections and are imaged while perfused with blood with various degrees of oxygenation. Selective biopsies are taken from placentas after imaging with LOUIS for histological assessment and validation of OAT method for high resolution imaging of blood perfusion in tissue. In case difficulties are encountered with blood-perfused in ex vivo placental tissue, an alternative approach is used where the placenta is represented by a general phantom matrix (see above) and the blood vessels are made of ultrathin PTFE tubes (0.635 mm ID and 0.05 mm wall thickness), which is excellent for optical and optoacoustic simulations. The tubes are perfused with diluted heparinized blood with spatial density and hematocrit levels adequate to represent an overall blood fraction in the placenta. At least 3 phantom samples are created with slightly different properties to simulate patient-to-patient variations. The phantoms mimic the in vivo situation as closely as possible using placental perfusion models.

EXAMPLE 8

Validation of LOUIS Via Optoacoustic and Ultrasonic Imaging of the Placenta Phantoms In the past 2D OAT systems showed good performance in imaging of solid and liquid tissue phantoms and in vivo imaging of breast tissue and peripheral vasculature (15, 31). OAT and laser ultrasound induced artifacts may diminish the OAT contrast and impede accuracy of mapping functional characteristics of the placenta, however, technological and data processing solutions used in OAT breast imaging may be implemented to reduce those artifacts. The phantoms are imaged according to the institutionally approved protocol using each of the wavelengths specified in Example 4 as well as in an ultrasound imaging mode. If visible, strong OAT sources like individual small blood vessels, are identified within the placenta and analyzed for local contrast. The obtained maps of local blood contrast and oxygenation in placentas are analyzed and are validated versus controlled experimental settings. The results are coregistered OAT/US images of all the phantoms and correlation graphs between optoacoustically measured and controlled parameters demonstrating precision and accuracy of the proposed technique.

FIGS. 4A-4B demonstrate that while optoacoustic brightness decreases with depth, an optoacoustic tomography image of a blood vessel within a realistic tissue phantom is obtainable at a depth 60 mm obtained with high contrast and resolution.

EXAMPLE 9

Validation of LOUIS Via Optoacoustic and Ultrasonic Imaging in Live Tissue

LOUIS imaging system enables functional imaging of total hemoglobin and its oxygen saturation. Images of an artery and a vein in live tissue are produced at 757 nm (FIG. 5A) and at 1064 nm (FIG. 5B). Switching the laser wavelength from 757 nm to 1064 nm produces optoacoustic images that switch brightness from hemoglobin to oxyhemoglobin and thereby identify the vein and the artery.

The following references are cited herein.

1. Haws et al., BMC Pregnancy and Childbirth 9 Suppl 1, S5 (2009).
2. Smith, G. C. and Fretts, R. C. Lancet 370(9600):1715-1725 (2007).
3. Grivell et al., The Cochrane Database of Systematic Reviews, 1:CD007113 (2009).
4. Tache et al., Stem Cells and Development (2013).
5. Kakogawa et al., American Journal of Perinatology, 27(1):25-29 (2010).
6. Kakogawa et al., American Journal of Perinatology, 27(6):463-468 (2010).
7. Kakogawa et al., American Journal of Perinatology, 24(3):161-166 (2007).
8. Elsayes et al., Radiographics: a review publication of the Radiological Society of North America, Inc 29(5):371-1391 (2009).
9. Oraevsky, A. A. and Karabutov, A. A., Optoacoustic Tomography in Biomedical Photonics Handbook T. Vo-Dinh, Ed., pp. 34/31-34/34, CRC Press, Boca Raton—London—New York—Washington, D.C. (2003).
10. Oraevsky, A., *Optoacoustic Tomography of the Breast* in PhotOATcoustic imaging and spectroscopy L. Wang, Ed., Taylor and Francis Group, New York (2009).
11. Wang, L. V. and Hu, S., Science 335(6075):1458-1462 (2012).
12. Roggan et al., Journal of Biomedical Optics 4(1):36-46 (1999).
13. Cerussi, et al., Journal of Biomedical Optics 11(4): 044005 (2006).
14. Ermilov et al., Journal of Biomedical Optics 14(2): 024007 (2009).
15. Zalev et al., Proceedings SPIE 8223:82230A (2012).
16. Yaseen et al., Journal of Biomedical Optics, 15(2): 021310 (2010).
17. Zalev et al., Proc. SPIE 8581:858103 (2013).
18. Cox et al., Journal of Biomedical Optics, 17(6): 061202 (2012).
19. Laufer et al., Applied Optics, 49(8)1219-1233 (2010).
20. Cox et al., Journal of the Optical Society of America, 26(2):443-455 (2009).
21. Niederhauser et al., IEEE Transactions on Medical Imaging, 24(4):436-440 (2005).
22. Friebel et al., Journal of Biomedical Optics, 11(3): 34021 (2006).
23. Shaw et al., Journal of Biomedical Optics, 10(5): 051503 (2005).
24. Shaw et al., Journal of Biomedical Optics, 9(3):534-540 (2004).

25. Laufer et al., Physics in Medicine and Biology, 52(1):141-168 (2007).
26. Laufer et al., Advances in Experimental Medicine and Biology, 578:155-160 (2006).
27. Laufer et al. Physics in Medicine and Biology, 50(18): 4409-4428 (2005).
28. ANSI, "Americal National Standard for Safe Use of Lasers," Americal National Standards Institutes Z136.1, 6-24 (2007).
29. Mobley, J. and T. Vo-Dinh, T., *Optical Properties of Tissue* in Biomedical Photonics Handbook T. Vo-Dinh, Ed., pp. 2/1-2/75, CRC Press, Boca Raton—London—New York—Washington, D.C. (2003).
30. Brecht et al. Journal of Biomedical Optics, 14(6): 064007 (2009).
31. Fronheiser et al. Journal of Biomedical Optics, 15(2): 021305 (2010).
32. Su et al. Journal of Biomedical Optics, 17(10):101506 (2012).
33. Oraevsky et al., U.S. application Ser. No. 13/775,865.
34. L. Hanssen, Applied Optics 40(19):3196-3204 (2001).
35. Myren et al. Toxicology In Vitro: an nternational journal published in association with BIBRA 21(7):1332-340 (2007).
36. Mathiesen et al., Reproductive Toxicology, 30(1):138-146 (2010).
37. Mathiesen et al. Basic & Clinical Pharmacology & Toxicology, 105(3):181-187 (2009).
38. Schneider, H. and Huch, A., Contributions to Gynecology and Obstetrics, 13:40-47 (1985).

What is claimed is:

1. A dual modality imaging system for evaluating functional parameters of placental blood within displayed anatomical structures of placenta, comprising:
   a pulsed laser operable at multiple wavelengths in the near infrared spectral window of maximum tissue transparency and within an absorption spectrum of hemoglobin and oxy-hemoglobin, said laser rapidly switchable between different wavelengths in said spectral window;
   a multichannel optoacoustic-ultrasonic probe, comprising:
      a fiberoptic light delivery system comprising a fused circular input tip operable for maximum transmission and randomized output for wide-beam homogenous illumination;
      a multichannel ultrasound detection array of ultrawide-band ultrasonic transducers for detecting ultrasonic pulses either generated within the tissue or reflected within the tissue; and
      a housing;
   a multichannel electronic system comprising low noise ultrawide-band analog amplifiers, analog to digital converters and digital data acquisition, said multichannel electronic system configured to detect, amplify, digitize, process, and store optoacoustic and ultrasonic signals produced by the optical and ultrasonic pulses generated within the blood or tissue or both; and
   a computer in electronic communication with the multichannel electronic system and having at least one memory, processor, display, and network connection tangibly storing an algorithm comprising processor-executable instructions to calculate quantitative functional parameters of a total hemoglobin [tHb] and of blood oxygenation [SO2] normalized to an optical fluence distribution characterizing placental and uterine factors, and display quantitative functional optoacoustic images of the functional parameters within specific anatomical structures in the tissue that are visualized by ultrasound.

2. The dual modality imaging system of claim 1, wherein the near-infrared spectral window comprises wavelengths of about 740 nm to about 850 nm.

3. The dual modality imaging system of claim 1, wherein said ultrawide band ultrasonic transducers are piezoelectric transducers.

4. The dual modality imaging system of claim 1, wherein laser pulses generated by said pulsed laser are applied to a layer of material with a strong optical absorption and strong thermoelastic expansion.

5. The imaging system of claim 1, wherein the multichannel optoacoustic-ultrasonic probe is a handheld transabdominal optoacoustic ultrasonic probe or a handheld transvaginal optoacoustic ultrasonic probe.

6. The imaging system of claim 1, wherein frequencies of said ultrawide-band transducers are about 100 kHz to about 10 MHz.

7. The imaging system of claim 1, wherein said processor-executable instructions are executable to:
   obtain an ultrasound tomography image of the placenta or associated tissue in an area suspected for anatomical or functional abnormalities;
   obtain optoacoustic images using at least two wavelengths without a change of the optoacoustic-ultrasonic probe position;
   coregister said optoacoustic images with the ultrasound image;
   calculate the quantitative functional parameters normalized to an optical fluence distribution at each wavelength;
   display an ultrasonic image of anatomical tissue structures superimposed with the quantitative functional image of the total hemoglobin; and
   display an ultrasonic image of the anatomical tissue structures superimposed with the quantitative functional image of the blood oxygen saturation.

8. The imaging system of claim 1, wherein the tissue comprises placenta or umbilical cord or both.

9. The imaging system of claim 1, wherein the quantitative functional parameters are evaluated in real time within at most 100 milliseconds.

10. A method for evaluating functional parameters of placental blood in a subject in real time, comprising the steps of:
   positioning the optoacoustic-ultrasonic probe comprising the imaging system of claim 1 in contact with the subject;
   obtaining an ultrasound tomography image of anatomical tissue structures in an area suspected for anatomical or functional abnormalities with the optoacoustic-ultrasonic probe;
   obtaining optoacoustic images at multiple wavelengths without a change of the optoacoustic-ultrasonic probe position;
   coregistering the optoacoustic images with the ultrasound image; and
   calculating quantitative functional images of a total hemoglobin [tHb] and of blood oxygenation [SO2] normalized to an optical fluence distribution characterizing placental and uterine factors at each wavelength, thereby evaluating the functional parameters of placental blood.

11. The method of claim 10, further comprising:
displaying an ultrasonic image of the anatomical tissue structures superimposed with the quantitative functional image of the total hemoglobin; and
displaying an ultrasonic image of the anatomical tissue structures superimposed with the quantitative functional image of the blood oxygen saturation.

12. The method of claim 10, further comprising diagnosing and managing a pathophysiological condition associated with the placenta and extraplacental tissue based on the evaluation of the functional parameters.

13. The method of claim 12, wherein said conditions are abnormal perfusion and oxygenation, placental abruptions or are associated with effects of medications, smoking or exercise.

14. The method of claim 10, wherein the anatomical tissue structures are the placenta, the umbilical cord or both.

15. The method of claim 10, wherein the multiple wavelengths comprise a near infrared spectral range of about 750 nm to about 840 nm.

* * * * *